United States Patent [19]
Vancaillie

[11] Patent Number: 5,846,219
[45] Date of Patent: Dec. 8, 1998

[54] VARIABLE BACKFLOW SUCTION-HYDRAULIC CURET

[76] Inventor: Thierry G. Vancaillie, 133 Pin Oak Forest, San Antonio, Tex. 78232

[21] Appl. No.: 638,366

[22] Filed: Apr. 26, 1996

Related U.S. Application Data

[63] Continuation-in-part of Ser. No. 250,753, May 26, 1994, abandoned.

[51] Int. Cl.⁶ ..................................................... A61M 1/00
[52] U.S. Cl. ................................ 604/35; 604/19; 604/27; 604/49; 604/54; 604/264
[58] Field of Search ................................ 604/19, 22, 27, 604/35, 49, 54, 264, 280, 902

[56] References Cited

U.S. PATENT DOCUMENTS

| | | |
|---|---|---|
| 2,531,730 | 11/1950 | Henderson . |
| 3,495,593 | 2/1970 | Snyder . |
| 3,636,940 | 1/1972 | Gravlee . |
| 3,774,613 | 11/1973 | Woods, Jr. et al. . |
| 4,403,983 | 9/1983 | Edelman et al. . |
| 4,493,694 | 1/1985 | Wuchinich ................................. 604/22 |
| 4,578,058 | 3/1986 | Grandon . |
| 4,690,672 | 9/1987 | Veltrup . |
| 4,913,698 | 4/1990 | Ito et al. . |
| 4,935,003 | 6/1990 | Gainutdinova et al. . |
| 4,958,901 | 9/1990 | Coombs . |
| 5,084,013 | 1/1992 | Takase . |
| 5,122,115 | 6/1992 | Marks . |
| 5,163,433 | 11/1992 | Kagawa et al. ..................... 128/660.01 |
| 5,197,949 | 3/1993 | Angsupanich ............................. 604/35 |
| 5,203,769 | 4/1993 | Clement et al. . |
| 5,318,518 | 6/1994 | Plechinger et al. . |
| 5,320,599 | 6/1994 | Grep et al. . |
| 5,336,170 | 8/1994 | Salerno et al. . |
| 5,562,609 | 10/1996 | Brumbach ................................. 604/22 |

OTHER PUBLICATIONS

Brochure, "Pulsavac Wound Debridement System" manufactured by Zimmer, Inc., Dover, Ohio (1989).

*Primary Examiner*—Wynn Wood Coggins
*Assistant Examiner*—Cris L. Rodriguez
*Attorney, Agent, or Firm*—Fish & Richardson P.C.

[57] ABSTRACT

A variable backflow suction-hydraulic curet for mobilizing and evacuating tissue in a patient requiring such tissue removal. The variable backflow suction-hydraulic curet combines three modes of action to effect tissue removal while minimizing damage to underlying or adjacent tissue. The three modes of action are tissue mobilization through mechanical contact, through a variable pressurized fluid stream, and through suction-induced scavenging of mobilized tissue. Suction-induced scavenging of mobilized tissue occurs when a partial vacuum is applied to mobilized tissue through a suction tube within the curet. Movement of fluid and tissue particulates through the suction tube is enhanced by a variable pressurized fluid backflow through the suction tube which tends to further fluidize particulates and to increase the velocity of evacuation fluid flow. Variable features of the curet fluid flows are responsive to curet positioning and to vacuum applied to the suction tube vacuum port.

16 Claims, 5 Drawing Sheets

VARIABLE BACKFLOW SUCTION-HYDRAULIC CURET

This application is a continuation-in-part of application Ser. No. 08/250,753, filed 26 May 1994, abandoned.

BACKGROUND

1. Field of the Invention

The invention relates to methods and apparatus for curettage.

2. Techniques of Curettage

Curettage is a process of removing tissue from the walls of body cavities. For example, in the treatment of gynecologic conditions in a patient requiring endometrial curettage, a curet is commonly used to mechanically scrape the superficial layers (i. e., the stratum spongiosum and stratum compactum) of the endometrium lining the uterine cavity. Removal of the loosened (mobilized) endometrial tissue is by conventional curet alone or with the aid of a vacuum source connected to a hollow curet. Use of either a conventional or vacuum curet, however, may result in damage to the endometrial surface remaining after curettage (i.e., the stratum basale) or even uterine perforation due to excessive contact force between the curet and the uterine cavity wall.

Other problems with conventional curettage may occur when tissue intended for removal is either inadvertently left (retained) within the uterus or removed in pieces which tend to clog the curet. Retained tissue may cause prolonged morbidity in the patient and represents a continuing risk of complications, while clogging of the curet prolongs the procedure, increases costs, and puts the patient at greater risk for retained tissue. Removing tissue by successive passes of a curet over the basal endometrial layer may reduce both the average size of tissue particles and the likelihood that tissue will be retained inappropriately. But successive passes of the curet may itself unduly prolong the procedure, as well as increasing the risk of tissue damage and the likelihood of subsequent medical complications with each pass.

Nevertheless, repeated passes of the curet may be required to gather tissue fragments which may be only lightly attached to the basal endometrium or may be lying free within the uterine cavity. While such tissue fragment removal should require less forceful curet-wall contact than initial tissue mobilization, optimal modulation of the curet-wall force during different phases of curettage requires substantial training and experience in the surgeon. Judgment errors leading to abrasion or puncture damage to the basal endometrium (due to too much contact force) or to retention of stratum spongiosum and perhaps stratum compactum within the uterine cavity (due to insufficient force or complete lack of contact) are not uncommon. In part, this is due to the different functional characteristics of conventional and vacuum curets.

A vacuum curet, for example, may be lightly applied to the endometrial lining, but the curet is often drawn into firmer tissue contact through forces created by the vacuum. Subsequently dragging the curet over the endometrial surface may effectively remove stratum spongiosum and stratum compactum, but it may also abrade the underlying basal endometrium. Attempts to reduce the potential for basal endometrial abrasion by lowering the amount of applied vacuum merely serve to reduce the beneficial scavenging effect for which the vacuum curet was chosen in the first place.

A conventional curet, in contrast, is not subject to vacuum-induced forces tending to draw it into excessively tight contact with the endometrial cavity wall. Instead the curet is entirely passive, requiring the surgeon to exert any required force through the curet handle. Further, because tissue fragments are not drawn to the curet by a partial vacuum, effective tissue removal with a conventional curet generally requires that the curet be brought into physical contact with virtually all tissue to be removed. Since even careful surgeons commonly fail to contact at least 20% of the endometrial wall during conventional curettage, the problem of retained tissue associated with use of a conventional curet becomes virtually unavoidable.

Thus, effective use of either a conventional or vacuum curet for endometrial curettage requires substantial surgical skill to avoid complications due either to clinically significant endometrial damage or excessive retained stratum spongiosum and stratum compactum. A new curet designed for effective vacuum scavenging of tissue fragments, with a reduced potential for suction-induced abrasion of an underlying body cavity wall, could reduce postoperative morbidity. Similarly, a new curet, preferably incorporating self-cleaning action and requiring less forceful and/or less comprehensive curet-wall contact during tissue removal, could also tend to improve the safety and efficacy of procedures involving curettage.

SUMMARY OF THE INVENTION

The present invention comprises methods and apparatus related to a variable backflow suction-hydraulic curet (SHC) which is intended for use in place of both conventional and vacuum curets to facilitate scavenging of tissue fragments, with a reduced potential for suction-induced abrasion of underlying tissue. The SHC comprises a suction tube coupled to at least one hydraulic tube. The suction tube comprises a distal suction tip portion spaced apart from a proximal suction port, the suction tip portion comprising an entry orifice and at least one air bleed orifice, and the entry orifice substantially defining a suction tip plane. The hydraulic tube comprises a distal hydraulic tip spaced apart from a proximal hydraulic port, the distal hydraulic tip being positioned to direct at least a portion of a fluid stream exiting (substantially tangentially to the hydraulic tip bore) from the hydraulic tip past (that is, proximate to) at least one of the air bleed orifices. In flowing past an air bleed orifice, at least one of the exiting fluid streams is variably redirected by fluid flow (which occurs in use as described herein) through the air bleed orifice. Additionally, a SHC comprises at least one hydraulic flow diverter coupled to the suction tube proximate at least one air bleed orifice, the hydraulic flow diverter comprising a flow reversal vane positioned to variably intercept (and thus variably redirect) at least a portion of at least one exiting fluid stream. Each SHC hydraulic flow diverter may additionally comprise at least one mobilization flow vane positioned to variably intercept (and thus variably redirect) at least a portion of at least one exiting fluid stream.

A preferred embodiment of the SHC may also be described as comprising a suction tube and at least one hydraulic tube substantially as described above, plus variable fluid stream redirection means comprising at least one air bleed orifice in the suction tip portion and at least one hydraulic flow diverter coupled to the suction tube proximate at least one air bleed orifice. As above, the diverter comprises a flow reversal vane positioned to variably intercept at least a portion of at least one said exiting fluid stream. Variable redirection of an exiting fluid stream is accomplished in the SHC by creating a variable partial vacuum within the suction tube (that is, creating a pressure gradient across the air bleed orifice) to variably draw a fluid stream through the air bleed orifice into the suction tube. The effect of this fluid stream as it moves substantially laterally across at least a portion of an exiting fluid stream from a distal hydraulic tip is to divert the exiting fluid stream by some amount which is a function of the substantially lateral fluid (control) stream momentum as well as the exiting fluid stream momentum (that is, involving momentum exchange between the two fluid streams). Note the efficiency of the fluid stream diversion function of the air bleed orifice (and/or other orifices analogous to control orifices of fluid amplifiers) may be significantly increased in certain preferred embodiments by creating fluid channels in which the Coanda effect may be employed as in a fluid amplifier or oscillator to augment the amplified action of the control stream(s).

The variable partial vacuum desired for preferred embodiments described herein may be created within the suction tube by modulating the vacuum source which in use would be connected to the proximal suction port, and/or by changing the proximity of the suction tip entry orifice to any structure (such as a tissue surface) which would alter the flow of air and/or other fluids into the entry orifice. In normal use, and even with substantially constant vacuum at a vacuum source, the sub-ambient pressure (that is, the partial vacuum) within the suction tube would be substantially continuously varying within the suction tip portion as the entry orifice is moved over a (relatively uneven) tissue surface and as varying quantities of water, blood, tissue fragments and air move through the entry orifice. Note that injection of air or other gaseous or liquid fluids from a proximal source (preferably outside the patient's body) through one or more separate fluid lumens (for carrying fluidic switching signals) can yield an even greater degree of operator control of fluid flows within and around the SHC suction tip portion.

The mean fraction of a fluid stream exiting a hydraulic tip and then experiencing substantial flow reversal (that is, a change in flow direction of at least about 95 degrees) by striking (that is, being intercepted by) a flow reversal vane may be altered through the combined influences of flow reversal vane position relative to the hydraulic tip bore tangent, the exiting fluid stream proximity to the air bleed orifice, fluid flow through the air bleed orifice, curet orientation, and exiting fluid stream velocity. While certain of these parameters may conveniently be predetermined, others may be altered during use to increase or decrease pressurized fluid backflow to achieve a desired balance of backflow flushing action with mobilization fluid flow directed to loosen tissue to be removed through the curet.

Note that if the suction tip entry orifice becomes relatively obstructed during use (for example, due to a heavy flow of blood and tissue particles), pressure within the suction tip portion will tend to decrease and fluid flow through the air bleed orifice will tend to increase (due to the greater pressure gradient across the air bleed orifice). Fluid flow through the air bleed orifice impinges substantially laterally on the exiting fluid stream, tending to cause angular deviation of the exiting fluid stream toward some maximum deviation in the manner of a fluid amplifier. A flow reversal vane positioned (as preferred) to intercept an increasing portion of the fluid stream as the fluid stream deviation increases toward its maximum will direct a pressurized backflow fluid stream of increasing flow rate into the suction tube, at least a portion of this pressurized backflow fluid stream being in a direction into the curet and away from the entry orifice. Such a pressurized backflow fluid stream tends to augment and further fluidize any particulate evacuation fluid flow present and also to increase its velocity into the curet and away from the entry orifice. To ensure that evacuation fluid flow is not further impeded in the suction curet, preferred embodiments will have a free entry orifice area less that any (more proximal) transverse cross-sectional area of the suction tube in question. This condition is readily achieved in practice due to the presence of the flow reversal vane (with its support structure(s)) substantially within the entry orifice, which effectively reduces the entry orifice free area.

Imposition of vacuum source modulation through the suction port of an SHC can produce substantially time-stable shifts in the average portion of an exiting fluid stream from a distal hydraulic tip which is intercepted by a hydraulic flow diverter. Since a falling pressure within a suction tip portion is generally associated with an increasing burden of fluids and particulates to be evacuated through the suction tip portion, preferred embodiments of the SHC include hydraulic flow diverters positioned so that at least one flow reversal vane will intercept an increasing portion of an exiting fluid stream from a hydraulic tip as the exiting fluid stream is further deviated by the action of a substantially laterally impinging fluid flow through an air bleed orifice. The increase in the portion of an exiting fluid stream thus intercepted by a flow reversal vane is substantially a (linear or nonlinear) function of the (substantially simultaneous) decrease in pressure within the suction tip portion with respect to ambient pressure around the tip (with a consequent increase in the pressure gradient across the air bleed orifice.

For convenience in this discussion, an increase in the intercepted portion of an exiting fluid stream is measured with respect to a baseline portion of the exiting fluid stream which is intercepted when the suction tip portion internal pressure is substantially equal to ambient pressure surrounding the suction tip portion (that is, when the pressure gradient across the proximate air bleed orifice is substantially zero). Note that to allow variability in the intercepted portion of an exiting fluid stream, the baseline intercepted portion is predetermined to be less than 100% for the expected SHC operating conditions (including velocity of the exiting fluid stream and orientation of the SHC). Note also that characteristic response of the SHC, as measured in percent change in the intercepted portion of an exiting fluid stream per unit of pressure gradient across the proximate air bleed orifice, may be predetermined in part by imparting a desired shape and orientation to the exiting fluid stream. For example, the stream may be substantially round, rectangular, triangular or trapezoidal, so that movement of the stream due to a substantially laterally impinging flow of (control) fluid (preferably primarily air) through the air bleed orifice results in the preferred characteristic response for each such combination of exiting fluid stream and proximate air bleed orifice (that is, the combination of an exiting fluid stream and the air bleed orifice predominantly affecting deviation of that stream as a function of fluid flow through the air bleed orifice). Note that in certain preferred embodiments, deviation of an exiting fluid stream may be affected by substantially lateral fluid flow through more than one air bleed orifice, and a substantially lateral fluid flow through a single air bleed orifice may affect deviation of more than one fluid stream exiting a distal hydraulic tip.

A distal hydraulic tip in the present invention is that portion of a hydraulic tube through which fluid entering the hydraulic port at a pressure above ambient exits the tube as a fluid stream which is substantially tangential to the bore of the hydraulic tip at the point of exiting. Similarly, the entry orifice of a distal suction tip portion in the present invention is that portion of a suction tube through which fluid (and tissue) adjacent the suction tip portion is permitted to enter the suction tube. Thus, a suction tip portion comprises an entry orifice, and the orifice (commonly of circular or elliptical shape) substantially defines a suction tip plane. Note that in embodiments wherein the entry orifice or a proximate structure is serrated, perforated or notched, the suction tip plane is substantially defined by the furthest extent of serrations or notches or material surrounding perforations.

A hydraulic tip proximate a suction tip portion (having a suction tip plane) may have an internal transverse cross-sectional shape (i.e., the internal shape viewed in a plane substantially perpendicular to the direction of fluid flow in the tip) substantially similar to that of the hydraulic tube to which it is coupled (e.g., round or oval in certain preferred embodiments). Substantially round hydraulic tips may include fluid stream rotating means comprising one or more lands and/or grooves in a substantially spiral configuration (analogous to rifling in a gun barrel) for imparting on a fluid stream substantially rotary motion about an axis substantially parallel to the direction in which the fluid stream as a whole is moving.

Conversely, a hydraulic tip cross-sectional shape may be altered from that of its associated hydraulic tube so as to impart a desired shape and direction(s) to a fluid stream exiting from the tip (e.g., a relatively thin, fan-or-disc-shaped stream, or a plurality of relatively high-velocity streams of substantially circular cross-section). In any case, the exiting fluid stream(s) (each exiting in a direction substantially parallel to the tangent to the bore of a distal hydraulic tip at the point of exit) preferably are oriented to facilitate mobilization of adjacent tissue with the fluid stream(s) and subsequent vacuum extraction of fluid and tissue. In certain preferred embodiments at least one mobilization flow vane is positioned to variably intercept at least a portion of at least one exiting fluid stream and redirect it to most effectively mobilize the tissue in question.

The choice of hydraulic tip cross-sectional (orifice) shape and exiting fluid stream direction for preferred embodiments of the present invention is influenced by several factors, including the type of tissue with which the SHC is expected to be used and the fluid pressure available at the hydraulic tip. For example, endometrial stratum spongiosum and stratum compactum are relatively friable and easily mobilized from the endometrial wall by a fan-or-disc-shaped fluid stream of relatively low pressure fluid impinging on the tissue surface at angles of (preferably) less than about 30 degrees. In contrast, mobilization during debridement of nonviable or infected tissue may be more easily accomplished in some patients with a relatively high-pressure, high-velocity, concentrated (e.g., round or oval cross-section) fluid stream impinging on the tissue surface at a preferred angle of from about ten degrees to about fifty degrees.

BRIEF DESCRIPTION OF THE DRAWINGS

FIGS. 8(A–F) schematically illustrate six embodiments respectively of the distal suction tip entry orifice, each orifice having a different pattern of serrations, perforations, or notches.

DETAILED DESCRIPTION

Figure 1:
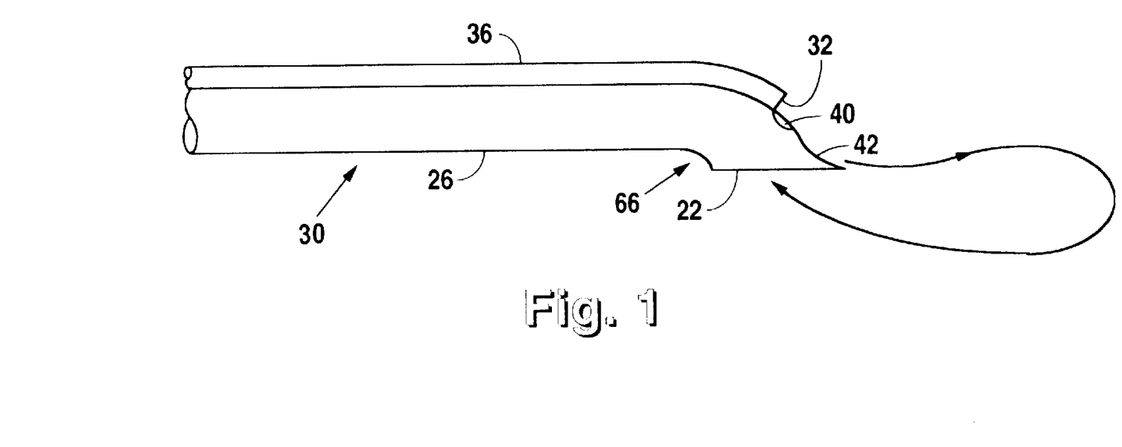
FIG. 1 schematically illustrates fluid flow in the region of suction and hydraulic tips and a mobilization flow vane in a variable backflow suction-hydraulic curet.
Figure 2:
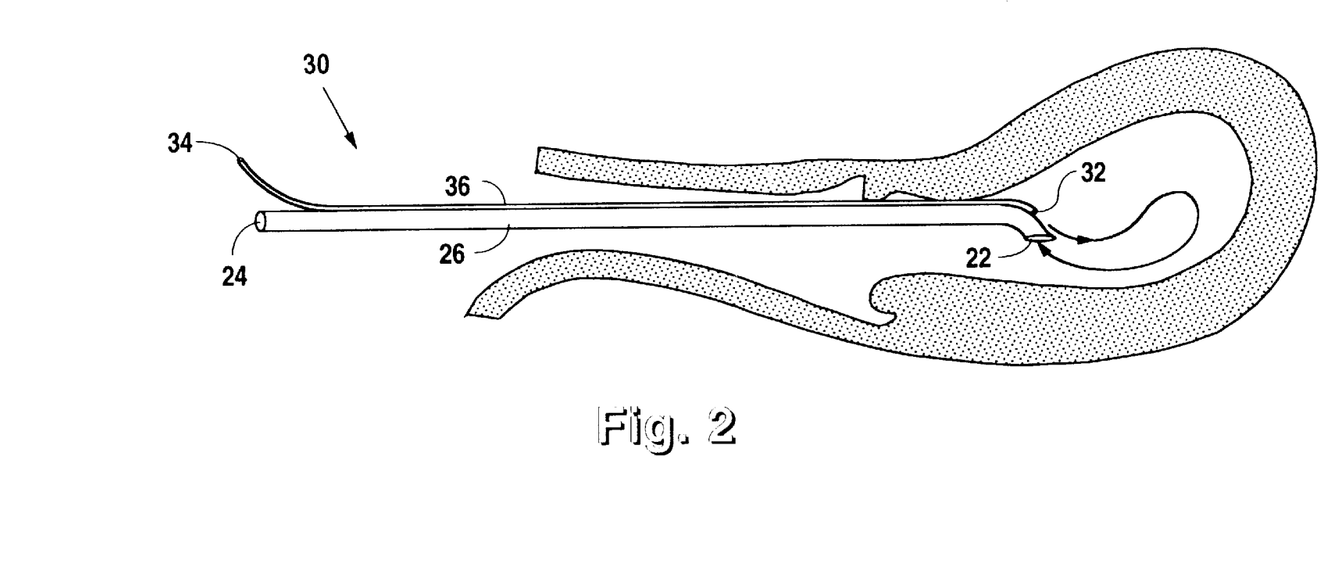
FIG. 2 schematically illustrates in partial cross-section a variable backflow suction-hydraulic curet as in FIG. 1 inserted within a uterus.

Referring to FIGS. 1 and 2, the suction-hydraulic curet (SHC) 30 comprises a suction tube 26 coupled to at least one hydraulic tube 36. A general fluid flow path from hydraulic tip 32 to suction tip entry orifice 22 is schematically illustrated by the heavy arrows in FIGS. 1 and 2. The suction tube 26 comprises a distal suction tip entry orifice 22 spaced apart from a proximal suction port 24, the suction tube 26 being substantially straight or (preferably) curvilinear (preferably curving about fifteen degrees between the suction tip entry orifice 22 and suction port 24). Each hydraulic tube 36 comprises a distal hydraulic tip 32 spaced apart from a proximal hydraulic port 34, at least a part of the hydraulic tube between the hydraulic tip 32 and the hydraulic port 34 being coupled (preferably by molding, gluing or welding) to at least a portion of suction tube 26. The distal suction tip entry orifice 22 is proximate at least one distal hydraulic tip 32 and at least one air bleed orifice 40. A fluid stream exiting distal hydraulic tip 32 will generally tend to flow along the tangent to the bore of hydraulic tube 36 at the exit point (that is, at hydraulic tip 32), and will preferably pass at least one air bleed orifice 40. At least one exiting fluid stream passes sufficiently close to at least one air bleed orifice 40 to be variably redirected by fluid flow through that air bleed orifice 40. Note that distal suction tip entry orifice 22 may exist in any of several embodiments, as in FIG. 8(A–F), and distal hydraulic tip 32 may exist in any of several embodiments, as in FIG. 7(1–6).

Figure 7:
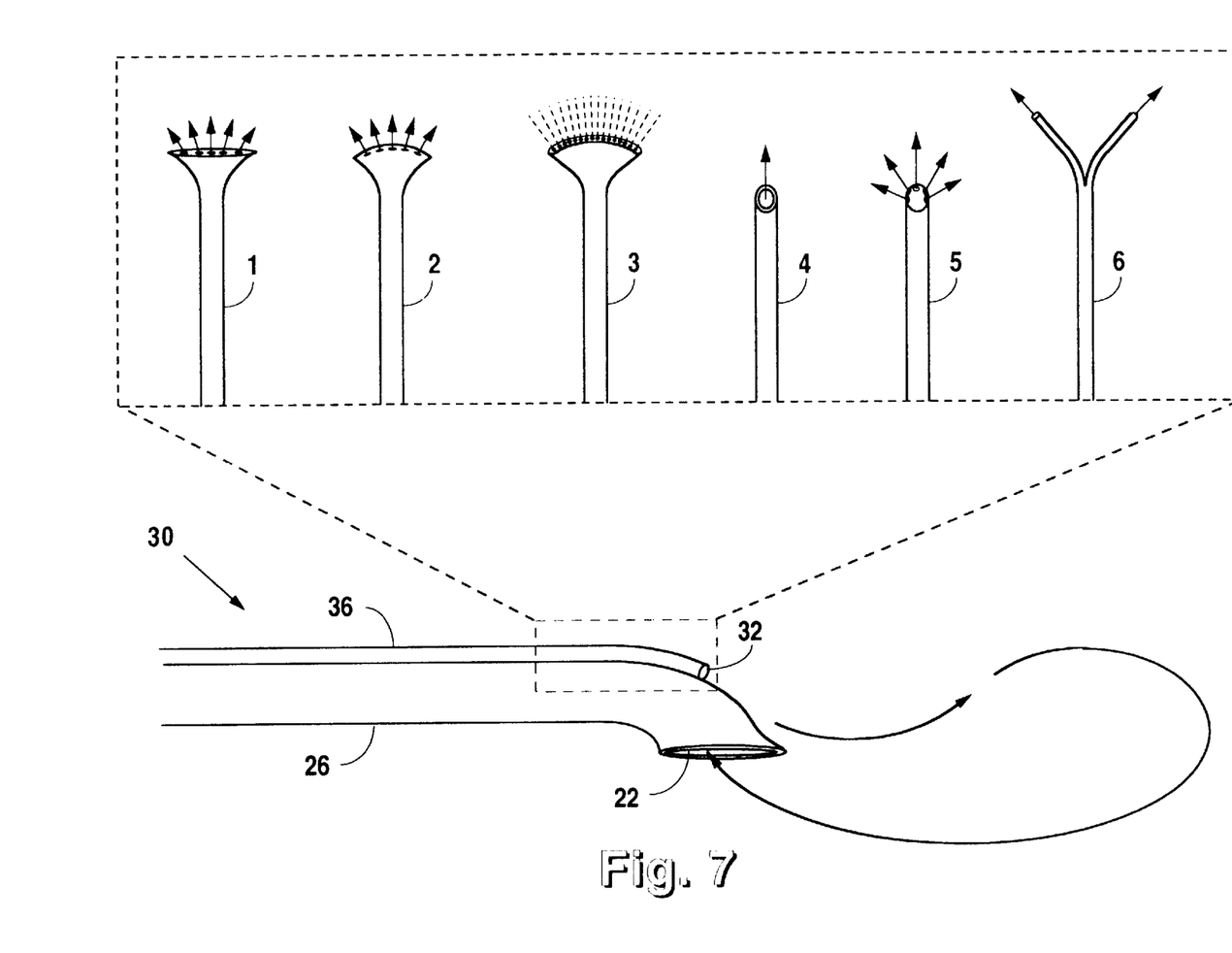
FIG. 7 schematically illustrates a suction-hydraulic curet as in FIG. 1, including schematic illustrations of six alternative embodiments of the distal hydraulic tip, each tip producing a different exiting fluid stream pattern.

Referring to FIG. 7, fan-or-disc-shaped fluid streams, as in FIG. 7(1), FIG. 7(2), and FIG. 7(3) may be obtained by use of a slit-shaped distal hydraulic tip orifice 32, i.e., a hydraulic tip orifice having a length substantially greater than its width. The slit may be substantially straight (as in FIG. 7(1)) or curved (as in FIG. 7(2)), the latter shapes including those of a circle sector or even a full circle. Note that the hydraulic tip orifice 32 may be intended to produce a single substantially concentrated fluid stream (as in FIG. 7(4)), a single substantially fan-shaped stream (as in FIG. 7(3) or a plurality of fluid streams (as in FIG. 7(1,2,5,6)) in a substantially linear or curvilinear array. Where a plurality of fluid streams exit distal hydraulic tip orifices 32, at least one hydraulic tip will be positioned to direct at least a portion of a fluid stream past an air bleed orifice 40 for redirection by fluid flow through the air bleed orifice 40.

Figure 5:
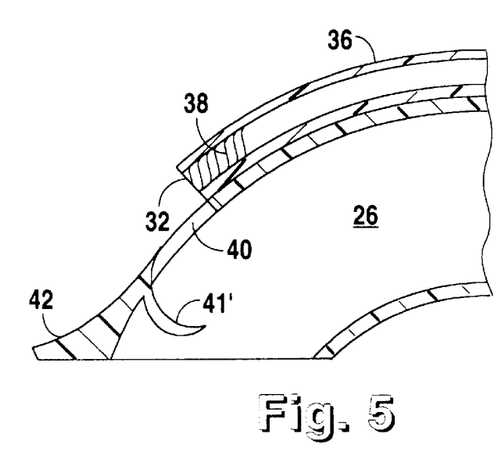
FIG. 5 schematically illustrates a cross-sectional view analogous to that of FIG. 3A, including integrated flow reversal and outward mobilization flow vanes.

Relatively high-velocity fluid streams may be so redirected and are preferably obtained through use of tip designs wherein the cross-sectional area is reduced proximate the location where fluid exits from the tip orifice, allowing for relatively low flow resistance losses in most of the hydraulic tube length. In certain embodiments, a plurality of nonuniformly sized orifices or single-orifice hydraulic tips (as in FIG. 7(4)) may be used to achieve a total desired fluid flow pattern, at least a portion of which will be subject to variable redirection under the influence of fluid flow through one or more air bleed orifices 40. Note that a fluid flow pattern including one or more fluid streams which rotate substantially about the (local) longitudinal axis of the stream may be desirable for mobilization of certain tissue types. The fluid stream rotating means schematically illustrated in FIG. 5 comprises at least one land 38 in hydraulic tube 36 proximate to distal hydraulic tip 32 in a substantially spiral configuration (analogous to rifling in a gun barrel) for imparting on a fluid stream substantially rotary motion about an axis substantially parallel to the direction in which the fluid stream as a whole is moving.

Figure 3:
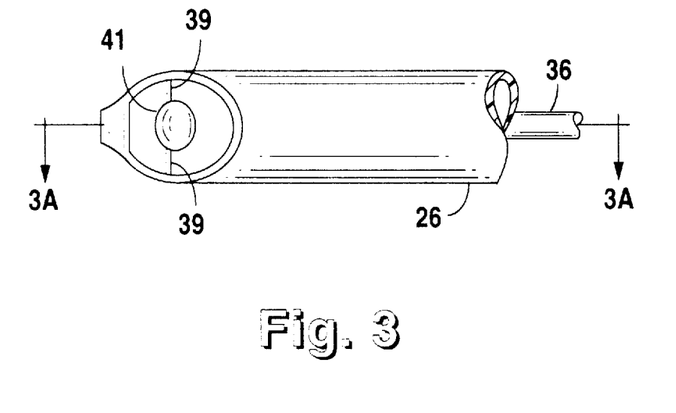
FIG. 3 schematically illustrates the entry orifice and distal portion of the variable backflow suction-hydraulic curet of FIG. 1.
Figure 3A:
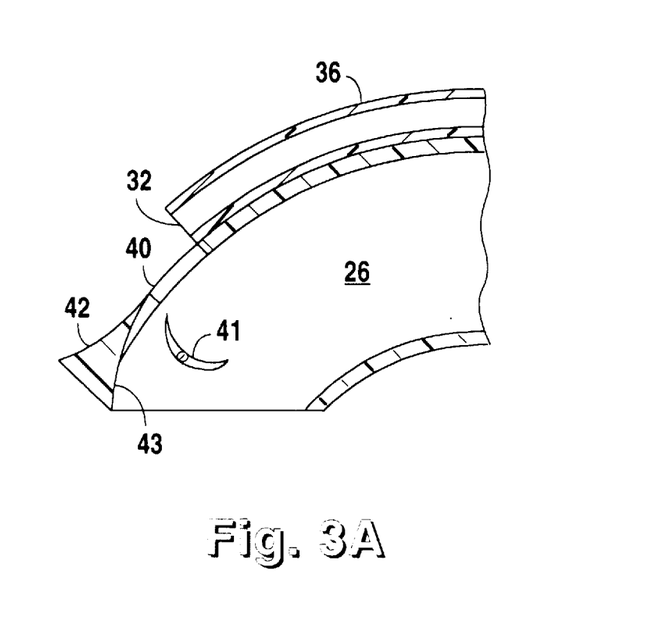
FIG. 3A schematically illustrates an enlarged portion of the indicated cross-sectional view of FIG. 3, including a flow reversal vane and axial and outward mobilization flow vanes.
Figure 4:
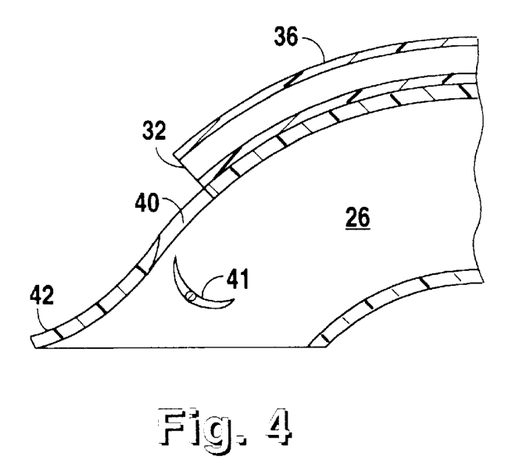
FIG. 4 schematically illustrates a cross-sectional view analogous to that of FIG. 3A, including spaced apart flow reversal and outward mobilization flow vanes.
Figure 6:
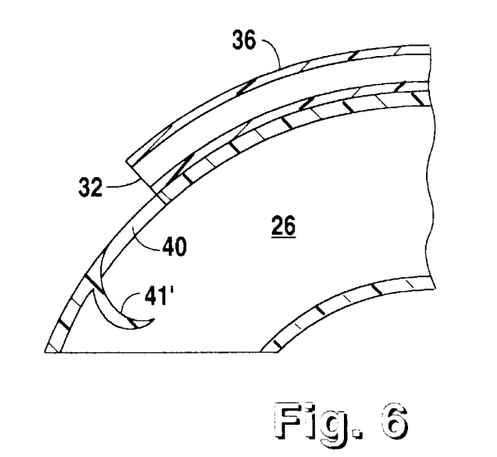
FIG. 6 schematically illustrates a cross-sectional view analogous to that of FIG. 3A, including an integrated flow reversal vane.

In preferred embodiments, the suction tube 26 will be oriented so as to place the distal suction tip entry orifice 22 adjacent to tissue which is to be mobilized and removed (shown schematically in FIG. 2). Mobilization and removal of the tissue using the SHC is preferably accomplished by a combination of effects: (1) from one or more fluid streams striking the tissue, (2) from physical contact of the SHC with the tissue, and (3) from the vacuum scavenging action by the suction tip portion of the SHC. Tissue mobilization may thus be optimized by directing at least one fluid stream so as to complement the mobilization forces of physical contact and vacuum scavenging and obtain a synergistic tissue mobilization effect. The combination of three effects to obtain tissue removal tends to separate tissue along natural tissue planes, thus minimizing trauma to underlying or adjacent tissue and reducing the likelihood of interoperative and postoperative complications. And since at least one fluid stream is subject to redirection under the influence of fluid flow through at least one air bleed orifice, a tissue mobilizing fluid stream can be increased, decreased and/or changed in direction through the control mechanisms described herein. Thus, the SHC can be more versatile in a range of applications than conventional curets.

Where tissue planes are relatively well defined, synergistic tissue mobilization may be observed when fluid is preferably directed in a relatively thin fan-or-disc-shaped stream (as in FIG. 7(1–3)), the fluid flow plane of which is oriented substantially parallel to the tissue planes in question. Mobilization fluid flow planes or fluid stream directions can be altered by variably redirecting portions of a fluid stream to a mobilization vane 42 directed substantially tangentially outward (or inward), a mobilization vane 43 directed inward (or outward), or substantially directly from a distal hydraulic tip to a tissue surface (as in FIG. 6). In all cases, at least a portion of at least one fluid stream exiting a hydraulic tip will be variably redirected to a flow reversal vane 41,41'. Flow reversal vane 41,41' may be supported within the distal suction tip entry orifice 22 by supporting members 39 or analogous structures, or may be integrated into the wall structure of suction tube 26 as in FIGS. 5 and 6. Note that when present, mobilization fluid flow vanes may be spaced apart from a flow reversal vane (as in FIGS. 3A and 4) or integrated with a flow reversal vane (as in FIG. 5). By proper choice of mobilization vane configurations and spacings, fluid flow at moderate pressures can act to maintain or increase separation of the tissue along the tissue planes, while physical contact with the SHC and vacuum scavenging tend to enhance tissue separation (and thus tissue mobilization). Preferred fluid flow may be also be directed substantially perpendicularly or obliquely to local tissue planes as, for example, when debridement and/or removal of infected tissue are desired.

Any desired variably redirected fluid flow orientation may be used in a method for tissue removal by suction-induced scavenging in a patient having tissue to be removed. The method comprises directing a stream of pressurized variably redirected fluid from a SHC at the tissue to be removed, contacting the tissue to be removed with said SHC, and applying a partial vacuum through said SHC to the tissue to be removed to effect tissue removal by suction-induced scavenging.

Suction-induced scavenging takes place as fluid and mobilized tissue fragments are drawn by a partial vacuum in the suction tube 26 into the entry orifice 22 of the distal suction tip portion of an SHC. A partial vacuum is maintained in the suction tube 26 by coupling the proximal suction port 24 to a continuously evacuated piping system (not shown) like that conventionally available in an operating room (i.e., a facility vacuum system). The coupling of SHC and facility vacuum system would preferably be accomplished through a trap (not shown), wherein fluid and tissue fragments scavenged through the suction tube 26 would be retained for examination and later disposal.

The entry orifice 22 of a distal suction tip portion may be formed in preferred embodiments of the present invention by cutting a substantially cylindrical suction tube 26 at the tube's intersection with a mathematically described plane. To form an entry orifice 22, an intersecting plane is preferably not substantially perpendicular to the local suction tube bore tangent at the distal end (that is, the suction tip portion) of the suction tube. To form an oblique entry orifice, an intersecting plane is preferably oblique to the local tangent for the suction tube 26.

Figure 8A:
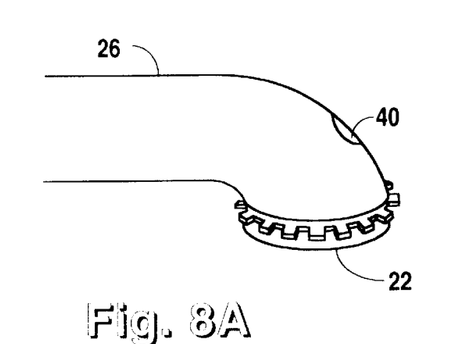
Figure 8B:
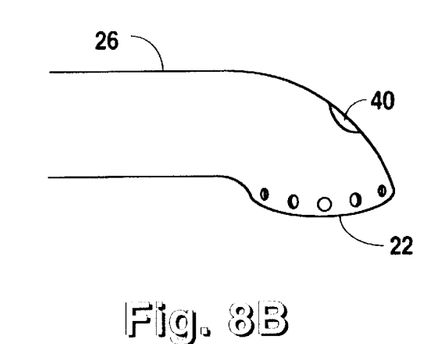
Figure 8C:
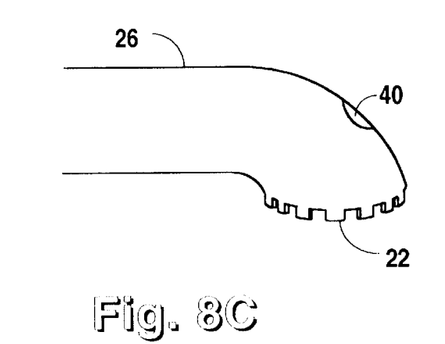
Figure 8D:
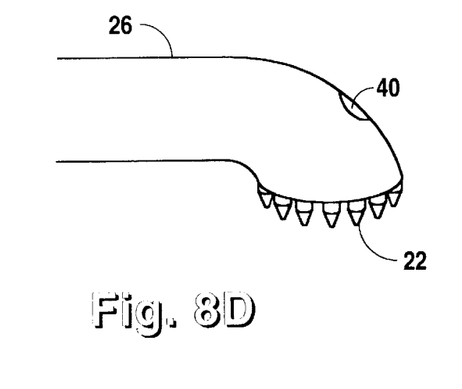
Figure 8E:
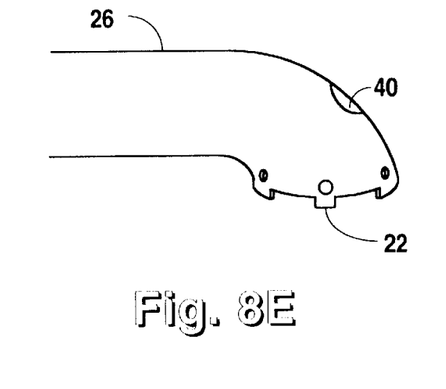
Figure 8F:
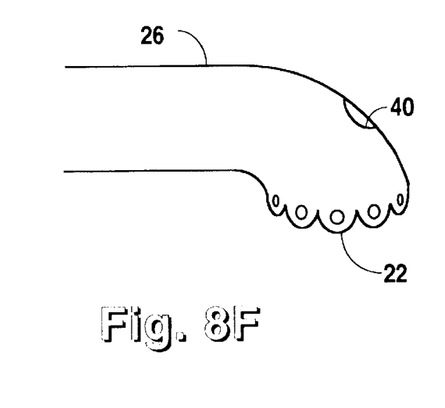

All suction tip entry orifices 22, whether comprising e.g., transverse, oblique or side orifices in SHC's of the present invention may, in certain preferred embodiments, comprise serrated orifices (as in FIG. 8D and/or perforated orifices (as in FIG. 8(B,E,F)) and/or notched orifices or structures (as in FIG. 8(C,E)). Modifications and combinations of these structures are also contemplated (as the scalloped, perforated orifice in FIG. 8F). Serrations and/or perforations and/or notches or modifications thereof may also appear on the edges of structures which are substantially rigidly affixed (e.g., as by welding or gluing) to a portion of a suction tip entry orifice (e.g., a serrated edge structure may be affixed to a suction tube at a location proximate to but spaced apart from the suction tip orifice on a suction tube, as in FIG. 8A). Orifice edges and structures bearing serrations and/or perforations and/or notches perform the functions of increasing the potential for mobilization of tissue in physical contact with a SHC, reducing the likelihood of a suction tip orifice being drawn into excessively firm contact with a tissue surface by vacuum-induced forces, and redirecting the flow of fluid from a hydraulic tip 32 to adjacent tissue. All of these functions may optionally be performed by other components of the SHC, but in certain embodiments, serrations and/or perforations and/or notches may be preferred. If present, serrations and/or perforations and/or notches may be applied to only a portion of available edge and/or structure, and need not be regular in shape. Note that at least one air bleed orifice 40 is proximate each suction tip entry orifice 22, although none are visible in the views of FIGS. 2, 3 or 7. Note also that one or more hydraulic tubes 36 may be present on (that is, coupled to) substantially any portion of a suction tube 26 between the suction port 24 and an air bleed orifice 40. The hydraulic tubes in the Figures are positioned for ease of illustration and not to indicate a preference for a particular positions and/or orientations.

What is claimed is:

1. A curet, comprising:
   a suction tube, said suction tube comprising a distal suction tip portion spaced apart from a proximal suction port, said suction tip portion comprising an entry orifice and at least one bleed orifice;
   at least one hydraulic tube coupled to said suction tube, each said hydraulic tube comprising a distal hydraulic tip spaced apart from a proximal hydraulic port, and configured to allow a fluid stream to flow through the hydraulic tube from the hydraulic port to the hydraulic tip and exit the hydraulic tube through the hydraulic tip, said distal hydraulic tip being positioned to direct at least a portion of the fluid stream exiting said hydraulic tip past at least a first orifice of said at least one bleed orifice; and
   at least one hydraulic flow diverter coupled to said suction tube proximate said first orifice, said diverter comprising a flow reversal vane positioned at least partially within the suction tube to variably intercept at least a portion of said exiting fluid stream.

2. The curet of claim 1, wherein said at least one hydraulic flow diverter additionally comprises at least one mobilization flow vane positioned to variably intercept at least a portion of at least one said exiting fluid stream.

3. The curet of claim 2 wherein a first such mobilization flow vane is directed substantially tangentially outward from said distal suction tip portion.

4. The curet of claim 2 wherein a first such mobilization flow vane is directed substantially inward from said distal suction tip portion.

5. The curet of claim 2 wherein a first such mobilization flow vane is directed substantially tangentially outward from said distal suction tip portion and a second such mobilization flow vane is directed substantially inward from said distal suction tip portion.

6. A method for evacuating tissue to be removed from a patient using a pressurized variable curet flush flow in the current of claim 2, the method comprising
   directing a stream of pressurized fluid into at least one said hydraulic tube through said proximal hydraulic port, said fluid stream exiting from said distal hydraulic tip of at least one said hydraulic tube;
   intercepting at least a portion of said exiting fluid stream with said flow diverter;
   directing fluid flowing over said at least one mobilization flow vane at a portion of tissue to be removed for mobilizing the tissue;
   placing said suction tip entry orifice proximate the tissue to be removed to evacuate at least a portion of the tissue; and
   creating a variable vacuum within said suction tube variably draw a stream through said bleed orifice into said suction tube, said stream variably influencing said exiting fluid stream divert said exiting fluid stream toward said flow reversal vane to create a pressurized variable curet flush flow.

7. A method for mobilizing tissue for removal using the curet of claim 2, the method comprising:
   directing a stream of pressurized fluid into at least one said hydraulic tube through said proximal hydraulic port, said fluid stream exiting from said distal hydraulic tip of at least one said hydraulic tube;
   intercepting at least a portion of said exiting fluid stream with said flow diverter;
   directing fluid flowing over said at least one mobilization flow vane at a portion of tissue to be removed for mobilizing the tissue.

8. The curet of claim 1 wherein at least one such distal hydraulic tip comprises a slit-shaped orifice.

9. The curet of claim 1 wherein at least one such distal hydraulic tip comprises fluid stream rotating means.

10. The curet of claim 1 wherein at least one such distal hydraulic tip comprises a plurality of orifices.

11. The curet of claim 1 wherein said entry orifice is serrated.

12. The curet of claim 1 wherein said entry orifice is notched.

13. The curet of claim 1 wherein said entry orifice is perforated.

14. A method for creating a pressurized variable curet flush flow in the curet of claim 1, the method comprising
   directing a stream of pressurized fluid into at least one said hydraulic tube through said proximal hydraulic port, said fluid stream exiting from said distal hydraulic tip of at least one said hydraulic tube;
   intercepting at least a portion of said exiting fluid stream with said flow diverter;
   creating a variable partial vacuum within said suction tube to variably draw a stream through said bleed orifice into said suction tube, said stream variably redirecting said exiting fluid stream toward said flow reversal vane to create a pressurized variable curet flush flow.

15. A curet, comprising:
   a suction tube, said suction tube comprising a distal suction tip spaced apart from a proximal suction port, said suction tip comprising an entry orifice and at least one bleed orifice;
   at least one hydraulic tube coupled to said suction tube, each said hydraulic tube comprising a distal hydraulic tip spaced apart from a proximal hydraulic port, and configured to allow a fluid stream to flow through the hydraulic tube from the hydraulic port to the hydraulic tip and exit the hydraulic tube through the hydraulic tip, said distal hydraulic tip being positioned to direct at least a portion of a fluid stream exiting said hydraulic tip past at least a first orifice of said at least one bleed orifices, wherein at least some of the portion of the fluid stream is variably redirected by air flow through the first orifice; and
   at least one hydraulic flow diverter coupled to said suction tube proximate the first orifice, said diverter comprising a flow reversal vane positioned at least partially within the suction tube to variably intercept at least some of the portion of said fluid stream.

16. A curet, comprising:
   a suction tube, said suction tube comprising a distal suction tip portion spaced apart from a proximal suction port, said suction tip portion comprising an entry orifice and at least one bleed orifice;
   at least one hydraulic tube coupled to said suction tube, each such hydraulic tube comprising a distal hydraulic tip spaced apart form a proximal hydraulic port, and configured to allow a fluid stream to flow through the hydraulic tube from the hydraulic port to the hydraulic tip and exit the hydraulic tube through the hydraulic tip, said distal hydraulic tip being positioned to direct at least a portion of the fluid stream exiting said hydraulic tip past at least a first orifice of said at least one bleed orifice; and at least one hydraulic flow diverter coupled to said suction tube proximate said first orifice, said diverter comprising at least one mobilization flow vane directed substantially outward from said distal suction tip portion and positioned to intercept at least a portion of said exiting fluid stream.

* * * * *